(12) United States Patent
Wenz et al.

(10) Patent No.: US 9,149,652 B2
(45) Date of Patent: Oct. 6, 2015

(54) METHOD FOR TRANSPORTING RADIATION, APPLICATOR AS WELL AS RADIATION THERAPY DEVICE

(75) Inventors: Frederik Wenz, Heidelberg (DE); Dietrich Wolf, Oberkochen (DE); Norbert Reng, Heidenheim (DE); Holger Fuchs, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 1561 days.

(21) Appl. No.: 12/215,908

(22) Filed: Jun. 30, 2008

(65) Prior Publication Data
US 2009/0048478 A1 Feb. 19, 2009

(30) Foreign Application Priority Data
Jun. 29, 2007 (DE) .......................... 10 2007 030 317

(51) Int. Cl.
*A61N 5/00* (2006.01)
*A61N 5/10* (2006.01)

(52) U.S. Cl.
CPC ........................................ *A61N 5/10* (2013.01)

(58) Field of Classification Search
CPC ............. A61N 5/00; A61N 5/10; A61N 5/02; A61N 5/0601; A61N 5/1001; A61N 5/1002; A61N 2005/1003; A61N 5/1004; A61N 5/1027; A61N 5/1007; A61N 5/1015
USPC ....................... 600/1–8; 378/64, 65
See application file for complete search history.

(56) References Cited

U.S. PATENT DOCUMENTS

| | | | |
|---|---|---|---|
| 4,266,139 A | 5/1981 | Sportelli et al. | |
| 4,327,293 A | 4/1982 | Taumann | |
| 5,039,867 A | 8/1991 | Nishihara et al. | |
| 5,242,372 A | 9/1993 | Carol | |
| 5,429,582 A * | 7/1995 | Williams | 600/2 |
| 5,452,720 A | 9/1995 | Smith et al. | |
| 5,947,891 A | 9/1999 | Morrison | |
| 6,048,299 A | 4/2000 | Hoffmann | |
| 6,080,992 A | 6/2000 | Nonaka et al. | |
| 6,159,139 A | 12/2000 | Chiu | |
| 6,421,416 B1 | 7/2002 | Sliski et al. | |

(Continued)

FOREIGN PATENT DOCUMENTS

| | | |
|---|---|---|
| CA | 1097437 A2 | 3/1981 |
| DE | 4413490 C1 | 8/1995 |

(Continued)

*Primary Examiner* — Christine H Matthews
(74) *Attorney, Agent, or Firm* — Kriegsman & Kriegsman

(57) ABSTRACT

Among other things, a method for transporting radiation to a body region is described, wherein, in a first step, a canal is formed up to the body region to be irradiated and wherein, in a second step, an applicator (10) which is fitted to the diameter of the canal is introduced into the canal in order to guide a probe tip. Advantageously, applicator (10) is formed for use with a radiation therapy device for producing a defined radiation dose for irradiating a body region, whereby applicator (10) has a base body (11) with a foot region (12) for the uptake of at least one component of a radiation therapy device (30), a cylindrical guide region (13) connecting thereto for the uptake of a probe tip of a radiation therapy device, whereby a transition region (14) is formed between the foot region (12) and the guide region (13), as well as a head region (15), which is formed at the distal end (21) of base body (11). The method can be utilized especially for the treatment of tumors in the vertebral column.

25 Claims, 3 Drawing Sheets

(56) References Cited

U.S. PATENT DOCUMENTS

| | | |
|---|---|---|
| 7,109,505 B1 | 9/2006 | Sliski et al. |
| 7,905,822 B2 * | 3/2011 | Patrick et al. .................... 600/8 |
| 2003/0209677 A1 | 11/2003 | Kumakhov et al. |
| 2007/0040127 A1 | 2/2007 | Brahme et al. |
| 2009/0209802 A1 | 8/2009 | Francescatti et al. |
| 2011/0215260 A1 | 9/2011 | Kleinwaechter et al. |
| 2011/0216885 A1 | 9/2011 | Kleinwaechter et al. |

FOREIGN PATENT DOCUMENTS

| | | |
|---|---|---|
| DE | 102008030590 A1 | 1/2009 |
| EP | 0259989 A1 | 3/1988 |
| EP | 1529554 A1 | 5/2005 |
| EP | 1826778 A2 | 8/2007 |

* cited by examiner

METHOD FOR TRANSPORTING RADIATION, APPLICATOR AS WELL AS RADIATION THERAPY DEVICE

The present invention first relates to a method for transporting radiation to a body region as well as a method for treating a vertebral body. Further, the invention relates to an applicator for use with a radiation therapy device for producing a defined radiation dose for irradiating a body region, having a base body with a foot region for the uptake of at least one component of a radiation therapy device, a cylindrical guide region connecting thereto for the uptake of a probe tip or a radiation source unit of a radiation therapy device, wherein a transition region is formed between the foot region and the guide region, and with a head region, which is formed at the distal end of the base body, as well as a radiation therapy device having a radiation source unit and having an applicator.

The present invention lies in the field of radiation therapy, and is particularly associated with the irradiation of tumors and the like.

In a number of tumors, metastases occur in the bone of the vertebral column, which can influence its stability to the extent that a bone fracture may occur. Treatment by means of a radiation therapy device can thus be performed both for healing as well as only for prolonging life.

A known solution for irradiation is postoperative, percutaneous irradiation (irradiation through the skin) of the vertebra after the removal of the tumor. A disadvantage in the case of this known solution consists of the fact that healthy tissue must also be irradiated up to the site of the tumor. This may lead to the possible consequence of tissue damage.

Another disadvantage of this known solution is that, since the irradiation dose to the vertebra is divided into several irradiation treatments, which can be drawn out over several weeks, for example, six weeks, radiation must be conducted until the entire dose has been administered. This represents an additional burden to the patient, since the patient is frequently greatly limited in his freedom of movement.

There is thus the need to be able to conduct the irradiation intraoperatively. In this way, the dose necessary for treatment will be administered during the surgery. Since the patient then no longer needs to be subjected to any further irradiation, his physical and also his psychological burden is reduced, which is accompanied by a clear improvement in his quality of life. Optionally, a dose can be administered intraoperatively (boost), in order to shorten the follow-up percutaneous irradiation time.

A solution for such intraoperative irradiation is described, for example, in U.S. Pat. No. 6,421,416 B1. This publication discloses a radiation therapy system for the treatment of breast cancer. The system comprises a radiation source unit in the form of an x-ray radiation source as well as a probe tip for emitting x-ray radiation. A target is found at the end of the probe tip. High-energy electrons are accelerated to this target. The electrons are halted abruptly at the target. X-ray radiation is formed in this way. The system makes possible an intraoperative radiation treatment, thus during the operation, directly after the tumor tissue has been removed.

The probe tip, which involves a radiation therapy probe, is inserted into an applicator. The applicator consists of a basic body that first has a foot region. This foot region can serve for taking up at least one component of the radiation therapy device. In addition, the applicator provides a guide region for taking up a probe tip, whereby this guide region can be formed cylindrically, for example. The probe tip is disposed in the applicator at a defined position. The guide region is very short in the known solution and is formed in the field surrounding a head region of the applicator. Between the foot region and the guide region there is found a long, conically running transition region, whose particular function is the shielding of the probe, particularly relative to the outside.

X-ray radiation is formed at the end of the probe tip—i.e., in the head region of the applicator—during the operation of the radiation source unit. When the probe tip is introduced into the applicator, X-ray radiation with an approximately spherical radiation profile is released in the center of the applicator head region. The head region of the applicator is preferably spherical in shape in the known solution. The size of the head region thus always corresponds to the typical size of tumors. After the tumor is removed, the applicator with the probe tip of a radiation therapy probe is introduced into the body tissue and the tumor bed can be irradiated with a radiation dose that is distributed in a spatially uniform manner.

The irradiation of body tissue "from the inside", when compared to irradiation through the tissue (percutaneous irradiation) has the additional advantage that it can be conducted with higher local radiation doses.

Due to the relatively large diameter of the applicator in its head region, the type of irradiation used in the known solution has the advantage that a local irradiation of surface regions can be conducted. The disadvantage in this known solution is that the applicator cannot be introduced into constricted regions of the body, for example, into canals (i.e., drilled canals). In particular, the known solution therefore cannot be inserted into the vertebral column for the treatment of tumors.

The problem of the present invention is to further develop a method for transporting radiation to a body region, a method for the treatment of a vertebral body, an applicator as well as a radiation therapy device of the type named initially in such a way that the above-described disadvantages can be avoided. In particular, a solution will be provided which permits an irradiation into narrowly constricted body regions and particularly into canals. The solution will be particularly suitable for application in the treatment of tumors in the vertebral column.

The problem is solved according to the invention by a method for transporting radiation, to a body region that is characterized in that, in a first step, a canal is formed up to the body region to be irradiated and that, in a second step, an applicator which is fitted to the diameter of the canal is introduced into the canal in order to guide a probe tip or a radiation source. The problem is also solved according to the invention by a method for treating a vertebral body, that is characterized by the following steps: a drilled hole is made in the vertebral body, this hole reaching up to the region to be treated; radiation is transported to the region to be treated by the aforementioned method for transporting radiation to a body region, wherein an applicator which is fitted to the diameter of the canal is introduced into the canal in order to guide a probe tip or a radiation source unit, wherein radiation is produced by the radiation source unit and is transported to the region to be treated by means of the applicator, and whereby, the region to be treated is irradiated with radiation; and after terminating the treatment of the vertebral body, the applicator is removed from the drilled hole and subsequently the vertebral body is stabilized. In addition, the problem is also solved according to the invention by an applicator for use with a radiation therapy device for producing a defined radiation dose for irradiating a body region, the applicator having a base body with a foot region for the uptake of at least one component of a radiation therapy device, a cylindrical guide region connecting thereto for the uptake of a probe tip or a radiation source unit of a radiation therapy device, wherein a transition region is formed between the foot region and the guide region, and with a head region, which is formed at the distal end of the base body, the applicator characterized in that the diameter of the guide region is smaller than or equal to the diameter of the foot region and that the length of the guide region is longer than or equal to the length of the transition region. Additionally, the problem is also solved according to the invention by a radiation therapy device having a radiation source unit and having an applicator, the applicator having a base body with a foot region for the uptake of at least one component of a radiation therapy device, a cylindrical guide region connecting thereto for the uptake of a probe tip or a radiation source unit of a radiation therapy device, wherein a transition region is formed between the foot region and the guide region, and with a head region, which is formed at the distal end of the base body, the applicator characterized in that the diameter of the guide region is smaller than or equal to the diameter of the foot region and that the length of the guide region is longer than or equal to the length of the transition region.

Other features and details of the invention result from the subclaims, the description, as well as the drawings.

Features and details, which are described in connection with the applicator according to the invention, thus apply also, of course, to the radiation therapy device according to the invention as well as to the two methods, and vice versa. Features and details, which are described in connection with the radiation therapy device according to the invention, thus apply also, of course, to the applicator according to the invention as well as to the two methods, and vice versa. Finally, features and details, which are described in connection with the two methods according to the invention, apply also, of course, to the applicator according to the invention as well as to the radiation therapy device according to the invention, and vice versa. Naturally, features and details, which are described in connection with the method for transporting radiation to a body region according to the invention apply also, of course, to the method for the treatment of a vertebral body, and vice versa.

According to the first aspect of the invention, a method for transporting radiation to a body region is provided, which is characterized in that, in a first step, a canal is formed up to the body region to be irradiated and that, in a second step, an applicator which is fitted to the diameter of the canal is introduced into the canal in order to guide a probe tip or a radiation source unit.

Advantageously, the canal can be reinforced by a guide tube, at least in regions. A small tube that fits into the canal is thus introduced, this tube reinforcing the canal, at least in certain segments. Optionally, a small guide tube with a larger diameter than the guide region of the applicator can be placed in the prepared canal. The guide region of the applicator is guided into this small guide tube, which makes possible a more precise placement and secure movement of the applicator tip in the center of the tumor.

Advantageously, an applicator can be introduced into the canal, which is shaped for use with a radiation therapy device for producing a defined radiation dose for irradiating a body region, whereby the applicator has a base body with a foot region for the uptake of at least one component of a radiation therapy device, a cylindrical guide region connecting thereto for the uptake of a probe tip or a radiation source unit of a radiation therapy device and a head region, which is formed at the distal end of the base body.

Preferably, a transition region can be formed between the foot region and the guide region.

Advantageously, an applicator can be introduced into the canal, wherein the diameter of the guide region is smaller than the diameter of the foot region and wherein the length of the guide region is longer than or equal to the length of the transition region. In another configuration, an applicator can be introduced into the canal, wherein the diameter of the guide region is equal to the diameter of the foot region and wherein the length of the guide region is longer than or equal to the length of the transition region.

Preferably, the applicator can be introduced by its guide region into the canal, in particular a drilled canal or a tissue punch. In the last-named case, an application can also be made in organs, access being advantageously gained through the tissue punch.

Optionally, a small guide tube with a diameter larger than the guide region of the applicator can be placed for a certain distance in the prepared canal. The guide region of the applicator is guided in this small guide tube, which makes possible a more precise placement and secure movement of the applicator tip into the center of the tumor.

Advantageously, an applicator having a transition region with a conical course, at least in regions, can be introduced into the canal. In another configuration, an applicator can be introduced into the canal, the applicator having a transition region with a support surface, at least in regions, for at least one component of a radiation therapy device. The inner diameter of the guide region advantageously can be directly connected to the support surface.

Preferably, an applicator can be introduced into the canal in which the inside space of the guide region has been formed cylindrically.

In another configuration, an applicator can be introduced into the canal, the guide region of the applicator having an outer diameter, which is fitted to the canal diameter.

Preferably, an applicator, in which the ratio of the length of the guide region to the outer diameter of the guide region is larger by a multiple, is introduced into the canal.

Advantageously, an applicator, which has at least one radiation filter element and/or at least one cooling device, can be introduced into the canal.

Preferably, the radiation that is transported to the body region is produced by means of a radiation therapy device, wherein the radiation therapy device has a radiation source unit and the applicator. For example, the radiation source unit can be introduced into the applicator and the radiation can be emitted in this applicator. In another configuration, the radiation source unit can be joined to a probe tip for emitting radiation, whereby the probe tip is introduced into the applicator.

Advantageously, the radiation can be produced via a radiation source unit, which is disposed in a housing for the uptake of the radiation source unit. For example, the housing can have an uptake piece projecting from the housing for accommodating at least the probe tip or components of the radiation source unit. Preferably, the applicator can be joined with the housing in a detachable manner via a foot region and/or via an adapter. Preferably, a front side of the uptake piece can be placed at a transition region of the applicator, preferably adjacent to the proximal end of a guide region of the applicator.

According to a second aspect of the invention, a method for treating a vertebral body is provided, which is characterized by the following steps: A drilled hole is made in the vertebral body, this hole reaching up to the region to be treated; radiation is transported to the region to be treated by a method for transporting radiation according to the invention as described above, wherein an applicator which is fitted to the diameter of the canal is introduced into the canal in order to guide a probe tip or a radiation source unit, wherein radiation is produced by the radiation source unit and is transported to the region to be treated by means of the applicator, and whereby the region to be treated is irradiated with radiation; after terminating the treatment of the vertebral body, the applicator is removed from the drilled hole and subsequently the vertebral body is stabilized.

Preferably, at least one section of the drilled hole is reinforced by a guide tube by introducing a fitted guide tube into the drilled hole. Optionally, this drilled canal is reinforced by a small guide tube that has been introduced over a certain distance, and this guide tube has a diameter larger than the guide region of the applicator.

Advantageously, the vertebral body can be stabilized by filling with bone cement. In another configuration, after removal of the applicator from the drilled hole, the vertebral body can first be aligned by introducing a balloon catheter and subsequently by filling with bone cement.

In the two methods according to the invention described above, a drilled hole or a tissue punch is made, into which an applicator is subsequently introduced. The applicator can advantageously be a component of a radiation therapy device that at least has a radiation source unit. For example, the radiation source unit can be found directly in the applicator. In another configuration, the radiation source unit can be joined with a probe tip for emitting radiation, whereby the probe tip is then introduced into the applicator. Reference is also made to the full content of the following description relative to the applicator according to the invention as well as to the description relative to the radiation therapy device according to the invention for the advantages, effects as well as mode of operation of the applicator and the radiation therapy device within the two methods according to the invention, in order to avoid repetition.

According to a third aspect of the invention, an applicator is provided for use with a radiation therapy device for producing a defined radiation dose for irradiating a body region, the applicator having a base body with a foot region for the uptake of at least one component of a radiation therapy device, a cylindrical guide region connecting thereto for the uptake of a probe tip or a radiation source unit of a radiation therapy device, wherein a transition region is formed between the foot region and the guide region, and with a head region which is formed at the distal end of the base body. The applicator is characterized according to the invention by the fact that the diameter of the guide region is smaller than or equal to the diameter of the foot region and that the length of the guide region is longer than or equal to the length of the transition region.

According to the present invention, an applicator is consequently provided for use with a radiation therapy device for producing a defined radiation dose for irradiating a body region, the applicator having a base body with a foot region for the uptake of at least one component of a radiation therapy device, a cylindrical guide region connecting thereto for the uptake of a probe tip of a radiation therapy device, wherein a transition region is formed between the foot region and the guide region, and with a head region which is formed at the distal end of the base body. The applicator is characterized according to the invention by the fact that the diameter of the guide region is as small as possible and that the length of the guide region is as long as possible in order to be able to provide irradiation inside the body.

The applicator, whose features the preamble are taken from U.S. Pat. No. 6,421,416 B, so that the disclosure content of this latter patent is incorporated to the full extent in the disclosure of the present invention, is used for the irradiation of body regions, i.e., of a human patient, whereby the invention is not limited to the possibility of irradiating specific body regions. Several advantageous, but nonexclusive examples of application are explained in more detail in the further course of the description.

The applicator provides a base body, which consists of a number of different regions. A first region is formed by the foot region. It serves for the uptake of at least one component of a radiation therapy device, for example, at least one probe tip component, which represents one component of the radiation therapy device. The construction of such a radiation therapy device is explained in connection with the second aspect of the invention which is discussed in more detail below. A largely cylindrical guide region is adjacent to the foot region and this guide region serves for the uptake and guidance of a probe tip. A transition region, whose configuration and function are explained in more detail below, is provided between the foot region and the guide region. Finally, at its distal end, the applicator provides a head region, by which the radiation required for an irradiation is released. At the distal end, there is generally found the end of the applicator that lies the furthest away from the view of a user, for example, a surgeon. The distal end thus preferably also represents the free end of the guide region of the applicator.

According to the invention, it is now provided that the guide region is configured in a particular manner.

First, it is provided that the diameter (outer diameter) of the guide region is smaller than the diameter (outer diameter) of the foot region. A reduction in diameter is thus provided in the applicator, so that the guide region can be introduced into substantially narrower body regions, for example, into canals. Advantageously, the diameter of the guide region can be dimensioned such that the guide region closely surrounds a probe element that has been introduced. The present invention is not limited to specific ratios by which the two diameters are related to one another.

In addition, it is also provided according to the invention that the length of the guide region is longer than or equal to the length of the transition region. It is particularly preferably provided that the length of the guide region is longer than the length of the transition region by a multiple. As will be explained more extensively in the further course of the description, it is particularly possible by means of such a configuration, that the applicator or its head region (and thus the radiation required for an irradiation) can also reach into very narrow body regions, for example, into canals. The present invention is not limited to specific ratios by which the two lengths are related to one another. It is particularly important that the length of the guide region is as long as possible, so that deeper lying body regions, or a vertebra can be irradiated—even in patients with a large body size.

The subject of the present invention is thus an applicator, which is designed in particular for the treatment and therapy of bone cancer. The applicator is shaped in such a way that, with a probe element found therein, i.e., a radiation therapy probe, or a radiation source unit found therein, it can be inserted into a thin canal, for example, a drilled canal. Further, it may also be used for the irradiation of organs, whereby access is gained, for example, through a tissue punch.

The applicator, in particular its guide region, is advantageously formed in such a way that it surrounds the probe element or the radiation source unit—preferably as closely as possible. The applicator thus has four basic functions. First, it protects the probe element or the radiation source unit from mechanical stress. Next, it provides for an accurate placement of the radiation source, i.e., an x-ray source, or the tip emitting radiation in the body region to be irradiated, i.e., a tumor bed. In addition, the applicator represents a sterile barrier between the probe of the x-ray source and the tissue, as long as the applicator is sterile. Finally, it assures by its construction that the emitted radiation dose obeys a specific distribution.

Advantageously, the guide region can be formed for introduction into a canal, in particular a drilled canal, a punched canal, or a similar structure. The applicator is thus shaped in such a way that it can be introduced through the drilled canal into the body region to be irradiated. The applicator is particularly advantageously shaped in such a way that it can be introduced into a vertebra. A prerequisite for this type of treatment is that the applicator, in particular, its guide region, is as long as possible, so that the site of irradiation can be reached even in patients of large body size. Another prerequisite is that the applicator, in particular, its guide region, is as thin as possible, so that it can be guided through the drilled canal to the site of irradiation.

Preferably, the transition region can have a conical course, at least in regions. Preferably, the transition region can take such a conical course that it decreases, viewed from the foot region, in the direction of the guide region at such an angle that the applicator is optimally adapted to the surrounding region. The decrease can thus be linear, but it may also contain regions that have a different gradient. In the last-named case, it is then preferably provided that the transition region, considered in its entirety, decreases with the above-described angles.

Advantageously, the transition region can have a support surface, at least in regions, for at least one component of a radiation therapy device. It can be particularly preferably provided that the inner diameter of the guide region is directly connected to the support surface. Therefore, the applicator can be configured as long and as thin as possible, and it must surround the structural space of the radiation therapy device as closely as possible at the foot of the applicator, which can be achieved by such a configuration.

In another configuration, the inside space of the guide region can be formed cylindrically. Here, it is particularly provided that the cylindrical inside space has a contour which is adapted to the probe element, which is introduced into the applicator. Here, it is particularly provided that the guide region surrounds the probe element as closely as possible, in order to keep the total thickness of the guide region as small as possible for the above-given reasons.

Advantageously, the guide region can have an outer diameter which is fitted to the diameter of a canal, i.e., a drilled canal. As was described further above, the applicator can be used in particular for a treatment in which the vertebral body, whose stability has been or could be adversely affected by a tumor, can be stabilized (kyphoplasty, vertebroplasty). For this purpose, a drilled hole is prepared through the vertebral body and the tumor is dissected out, as needed. Usually, the drill and the drilled canal are limited in their diameter. Subsequently, the vertebra is irradiated intraoperatively and locally with a radiation therapy device, for example, a radiotherapy device, with a dose that has been defined in advance. Before or after the irradiation, if it has already been greatly mechanically damaged, the vertebral body can be aligned again by means of a balloon catheter (balloon kyphoplasty). Lastly, the vertebra is stabilized, for example, by means of bone cement.

For this purpose, the applicator must be as long as possible, so that the site of irradiation can be reached even in patients of large body size. A second prerequisite is that the applicator is as thin as possible, so that it can be guided through the drilled canal to the site of irradiation.

It is preferably provided that the ratio of the length of the guide region to the outer diameter of the guide region is greater by a multiple.

Therefore, the length of the applicator can be varied, of course. However, it should not go below a specific length that is defined by the body of the patient. It must be assured that the applicator reaches the site of the treatment. Likewise, the thickness of the applicator can be varied. However, it should not exceed a specified thickness defined by the canal (for example, a drilled canal) and lastly specified by the tumor. Otherwise, the applicator could not be guided through the canal to the site of the irradiation.

For the treatment of a tumor, it is desirable that the irradiation is conducted by means of radiation (for example, X-ray radiation), whose quantum energy lies within specific threshold values. The reason for this is that low-energy radiation cannot penetrate far enough into body tissue and that high-energy X-ray radiation has a greater penetration depth. The biological effectiveness of X-ray radiation, for example, is dependent on wavelength.

Advantageously, the applicator can have at least one radiation filter element. For example, it may have an X-ray radiation filter. The radiation, e.g., X-ray radiation, is hardened by the filter. This means that longer-wave radiation (radiation with less photon energy) is absorbed and attenuated. In particular, the shorter-wave portion of the radiation enters into bone tissue through the applicator and penetrates to varying depth in the bone tissue, each time depending on the photon energy. For example, a defined dose distribution by depth in the tissue can also be assured by the absorption property of the filter element. A spatial dose distribution at the site of irradiation can be provided in advance by a special shaping of the filter element. Such a filter element is described, for example, in U.S. Pat. No. 6,421,416 B1, the disclosure content of which is incorporated in the description of the present invention.

The filter element preferably consists of a material, which absorbs at least parts of the radiation (e.g., X-ray radiation). It can have wall thicknesses with locally defined dimensions, whereby it particularly can have free-form surfaces. For example, it can be provided that the filter element is extended in the applicator in a rotationally symmetric manner around a longitudinal axis of the guide region. In this way, the filter element is disposed between the inner wall of the applicator and the outer wall of the probe element, so that it surrounds the probe element, at least in regions. It may be provided that the filter element is formed in one piece, e.g., in the form of a type of sleeve. Of course, the filter element may also consist of a number of different segments, whereby advantageously, two or more such segments are provided. Of course, applications are also conceivable, where only a segment of a filter element is provided, which then covers only a limited region. Also, the filter element can be configured and placed in such a way that an angle-dependent irradiation is possible.

The present invention is not limited to a specific number of filter elements or to specific configurations, sizes and mesh types of filter elements. These result rather from the desired type of application. For example, it might be provided that the filter element is formed as a sleeve that is open at the top and bottom, whereby a shielding laterally can been achieved in particular. The radiation can then enter via the upper opening and then proceed from the distal end of the guide region of the applicator into its head region. It would also be conceivable that the above-described sleeve is closed at its upper end and thus forms a type of cap, which surrounds on all sides the end region of the probe introduced into the applicator. In this way, with a suitable selection of material, a defined radiation laterally or upwardly can be achieved.

In another configuration, the applicator can have at least one cooling device. The cooling device primarily serves for the purpose of drawing off the heat that has arisen due to the radiation source (for example, an X-ray radiation source).

According to the fourth aspect of the invention, a radiation therapy device is provided, having a radiation source unit and having an applicator, whereby the applicator is formed in the above-described way according to the invention. In this respect, reference is made to the full extent to the above statements relating to the applicator.

In a way known in and of itself, the radiation therapy device provides a radiation source unit which is advantageously an X-ray radiation source. In addition, the device provides a probe tip joined to the radiation source unit, by means of which the radiation that is produced is emitted. According to one embodiment, the radiation source unit can be disposed inside the applicator. According to another embodiment, the radiation source unit can be joined with a probe tip for emitting radiation, whereby the probe tip is disposed inside the applicator.

Advantageously, the probe tip will only be plugged into the applicator or is plugged into it.

Further, a housing can be provided in order to take up at least the components of the radiation source unit.

Advantageously, the housing can have an uptake piece projecting from the housing for at least the components of the probe tip. If the applicator is mounted, it is particularly provided that the described uptake piece is/will be taken up by the foot region [of the applicator]. In this way, it can be assured that the structural space of the radiation therapy device (for example, of a radiotherapy device) is surrounded by the applicator as closely as possible at the foot of the applicator, and thus the applicator can be shaped as long and as thin as possible.

Preferably, the applicator can be joined to the housing, in particular, to the uptake piece, in a detachable manner via its foot region. This can be done in the most varied manner, so that the invention is not limited to specific types of fastening. For example, it might be provided that the joining is effected by means of a screw connection, in which the foot region of the applicator is screwed onto the housing, for example, onto the uptake piece. In another configuration, it would also be conceivable that the connection is effected by means of a catch connection, in which a catch piece is engaged in a slot corresponding thereto. In this case, the catch piece can be formed either in the applicator or, however, in the housing. Preferably, the catch piece is formed on the applicator, the slot then being found on the housing, for example, in the region of the uptake piece.

Preferably, the applicator can be joined in a detachable manner to the housing, in particular, to the uptake piece, via an adapter. The adapter has the task of joining the applicator to the housing, whereupon the applicator is not directly connected to the housing.

In another configuration, the front side of the uptake piece can be placed at the transition region of the applicator, preferably adjacent to the proximal end of the guide region of the applicator. The proximal end thus represents the end that lies closest to the the view of a user, for example, a surgeon. It thus represents an end lying opposite a distal end, which has been described further above. In this way, it can be assured that the structural space of the radiation therapy device (for example, of a radiotherapy device) is surrounded by the applicator as closely as possible at the foot of the applicator, and thus the applicator can be shaped as long and as thin as possible.

As has already been stated above, among other things, the invention relates to a method for transporting radiation to a body region, which is characterized in that, in a first step, a canal is formed up to the body region to be irradiated and that, in a second step, an applicator which is fitted to the diameter of the canal is introduced into the canal in order to guide a probe tip. Optionally, small guide tubes, which are introduced into the canal, can serve for specifying a direction when the applicator is introduced.

The method can preferably be utilized as a method for the treatment of bone cancer and metastases.

One treatment possibility is to remove tumors mechanically from the vertebral column in an operation and then to irradiate the vertebra still during the surgery, i.e., intraoperatively and locally with X-ray radiation, wherein the removal of the tumor need not necessarily be carried out. For this purpose, a drilled hole is prepared through the vertebral body and the tumor is dissected out (kyphoplasty, vertebroplasty). Usually, the drill and the drilled canal are limited in their diameter. Subsequently, the vertebra is irradiated intraoperatively and locally with a radiation therapy device, for example, a radiotherapy device, with a dose that has been defined in advance. Lastly, the vertebra is stabilized, for example, by means of bone cement.

The radiation therapy device, for example, a radiotherapy device, has a probe element, which emits radiation (for example, X-ray radiation) at its tip. The probe element is surrounded by an applicator, which primarily has three functions. It protects the probe element from mechanical stress, it assures an accurate placement of the radiation source (for example, an X-ray source), i.e., the tip emitting the radiation, in the tumor bed, and assures by its construction that the dose obeys a specific distribution.

The applicator is shaped in such a way that it can be introduced through the drilled canal into the vertebra to be irradiated. A prerequisite for this type of treatment is that the applicator is as long as possible, so that the site of irradiation can be reached at any time. A second prerequisite is that the applicator is as thin as possible, so that it can be guided through the drilled canal to the site of irradiation.

An applicator according to the invention as described above is preferably introduced into the canal, so that, in order to avoid repetition relative to the construction and mode of operation, reference is also made to the full content of the corresponding statements made above.

The radiation is preferably produced by means of a radiation therapy device according to the invention as described further above, so that, in order to avoid repetition relative to the construction and mode of operation, reference is also made to the full content of the corresponding statements made above.

An applicator according to the invention as described further above and/or a radiation therapy device according to the invention as described further above and/or a method according to the invention as described further above can particularly advantageously be used for the radiation therapy treatment of tumors in the vertebral column.

It is conceivable, of course, that the applicator and/or the radiation therapy device and/or the method for the treatment of tumors and metastases will be utilized in other regions of the body, for example, in other bones, or in places which lie deeper inside the body and/or which can be reached through a biopsy canal. Examples of such organs are liver, kidney and brain.

By intraoperative irradiation, the dose necessary for treatment is preferably administered completely during the operation. Since the patient either does not need to be subjected to further treatment or needs fewer treatments, his physical and psychological burden is reduced, which is accompanied by a clear improvement in his quality of life.

The invention will now be explained in more detail based on an embodiment example with reference to the attached drawings. Here:

Figure 1:
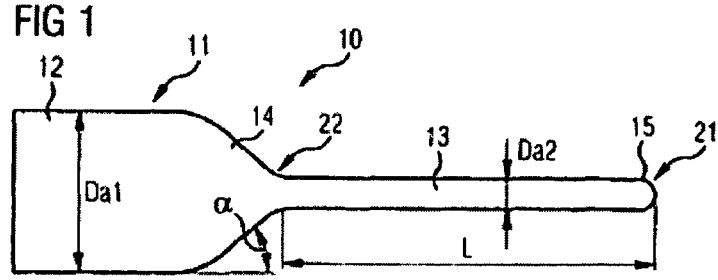
FIG. 1 shows the perspective outer appearance of an applicator according to the invention.
Figure 2:
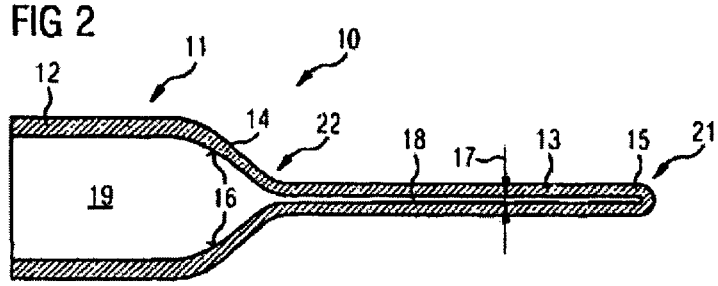
FIG. 2 shows the applicator shown in FIG. 1 in a cut-open vier.

An applicator 10 is shown in FIGS. 1 and 2, which is formed for taking up a probe element (not shown) of a radiation therapy device (also not shown). Applicator 10 provides a base body 11, which is made hollow on the inside, in order to take up different components of the radiation therapy device.

Base body 11 consists of three regions: a foot region 12, a guide region 13 and a transition region 14. At distal end 21 of base body 11, which also shows the distal end of guide region 13 in the Example, applicator 10 provides a head region 15 by means of which the radiation emitted by the incorporated probe element is delivered during operation.

Foot region 12 has an inside space 19, which is formed for the uptake of at least one component of a radiation therapy device. In particular, inside space 19 or foot region 12, respectively, has on its inner side a support surface 16 for at least one component of a radiation therapy device.

Guide region 13 has an inside space 18, which is formed cylindrically. The probe element required for emitting radiation is introduced into this cylindrical inside space 18. It is preferably provided that the guide region 13 surrounds the probe positioned therein as closely as possible. In addition, it is provided in the case of applicator 10, which is shown, that the inside diameter 17 of guide region 13 is directly connected to support surface 16.

Applicator 10 is utilized particularly advantageously for the treatment of tumors in the vertebral column, for which reason, a canal is first drilled to the site in the body that is to be irradiated. Applicator 10 or its guide region 13, respectively, is then introduced into this drilled canal.

A prerequisite for this type of treatment is that the applicator 10, or its guide region 13, is as long as possible, so that the site of irradiation can be reached at any time. A second prerequisite is that applicator 10, or its guide region 13, is as thin as possible, so that it can be guided through the drilled canal to the site of irradiation. It also must be assured that the structural space of the radiation therapy device (for example, of a radiotherapy device) is surrounded by applicator 10 as closely as possible at the foot of applicator 10, and thus applicator 10 can be shaped as long and as thin as possible. All of this can be achieved by the applicator 10 shown in FIGS. 1 and 2.

First, it is provided for this purpose that the diameter Da2 of guide region 13 is smaller than the diameter Da1 of foot region 12. In addition, it is provided that the length L of guide region 13 is as long as possible, in particular longer than or equal to the length of transition region 14. It is also particularly provided here that transition region 14 is kept as short as possible. This can be achieved if transition region 14 has a conical course, whereby the course decreases as steeply as possibly at an angle α such that the components found in the inside space 19 are surrounded as closely as possible. Additionally, the ratio of length L of guide region 13 to outer diameter Da2 of guide region 13 should be formed in such a way that guide region 13 is as long as possible, and at the same time is as thin as possible.

Figure 3:
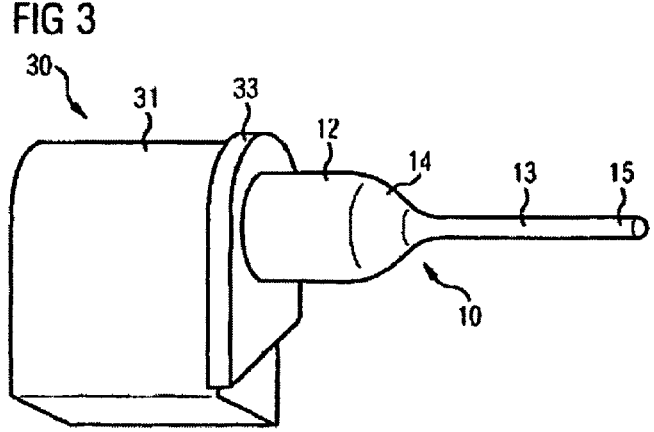
FIG. 3 shows a perspective outer view, in which the applicator is mounted on a housing of a radiation therapy device.
Figure 4:
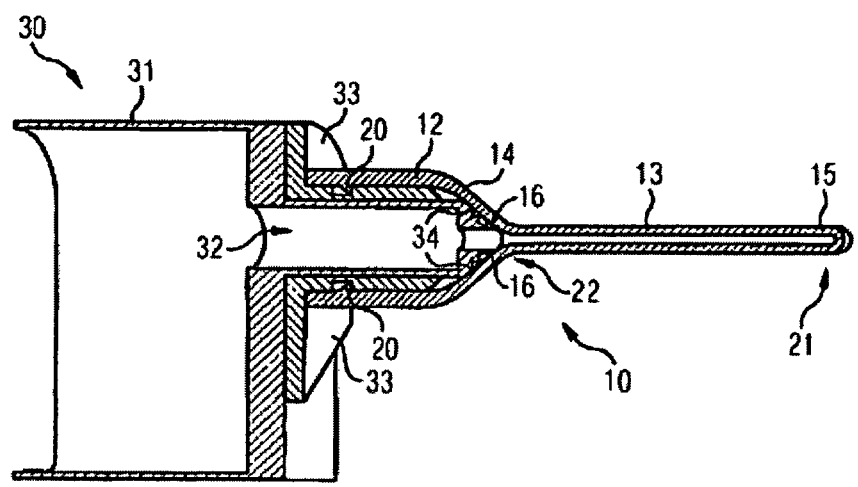
FIG. 4 shows the representation shown in FIG. 3 in a cut-open state.

A radiation therapy device 30 is shown in FIGS. 3 and 4, to which an applicator 10 as described in FIGS. 1 and 2 is attached in a detachable manner. FIGS. 3 and 4 only show a housing 31 of the radiation therapy device 30, which serves for the uptake of corresponding components. Housing 31 further has an uptake piece 32 projecting therefrom for at least the components of radiation therapy device 30. For example, it might be provided that components of a radiation source unit are accommodated in housing 31 and that components of a probe tip are accommodated in uptake piece 32. An opening is provided on front side 34 of uptake piece 32, by means of which the actual probe element can be plugged in.

The actual connection between housing 31 or uptake piece 32, respectively, and applicator 10 is effected in the example shown by means of an adapter 33, which is only optional, however. The connection shown in FIGS. 3 and 4 is made in a detachable manner, for example, by means of a catch connection 20. For this purpose, foot region 12 of applicator 10 provides corresponding catch pieces which can be engaged in uptake slots corresponding to these pieces in adapter 33. It can be provided that several slots and catch pieces are present. Likewise, it is possible, of course, that a catch piece extending over the entire circumference of foot region 12 of applicator 10 is engaged in a circular groove corresponding thereto.

If applicator 10 is joined to uptake piece 32 via adapter 33, uptake piece 32 is grasped by foot region 12 of adapter 10. In order to be able to provide a construction that is as compact as possible and in order to assure that guide region 13 of applicator 10 can be kept as long and as thin as possible, it is provided that front side 34 of uptake piece 33* is placed at transition region 14 of applicator 10, preferably adjacent to the proximal end 22 of guide region 13 of applicator 10. The region of the probe element extending outwardly from front side 34 of uptake piece 32 is thus found inside guide region 13 of applicator 10.

*sic; 32?—Translator's note.

A radiation therapy device 30 with a correspondingly shaped applicator 10, as shown in FIGS. 1 to 4, can be used advantageously for the treatment of bone cancer.

One treatment possibility is to remove tumors mechanically from the vertebral column during an operation and then to irradiate the vertebra still during the surgery, i.e., intraoperatively and locally with X-ray radiation, wherein the removal of the tumor need not necessarily be carried out. For this purpose, a drilled hole is first made through the vertebral body and the tumor is dissected out (kyphoplasty, vertebroplasty). Usually, the drill and the drilled canal are limited in their diameter. Subsequently, the vertebra is irradiated intraoperatively and locally with a radiation therapy device 30, for example, a radiotherapy device, with a dose that has been defined in advance. Lastly, the vertebra is stabilized, for example, by means of bone cement.

Radiation therapy device 30 has a probe element which emits radiation (for example, X-ray radiation) at its tip in the region of distal end 21 or head region 15 of applicator 10. The probe element is surrounded by applicator 10, which primarily has three functions. It protects the probe element from mechanical distortions, it provides for an accurate placement of the radiation source (for example, an x-ray source), i.e., the tip emitting the radiation, in the tumor bed, and it assures by its construction that the dose obeys a specific distribution.

Applicator 10 is shaped in such a way that it can be introduced by its guide region 13 through the drilled canal into the vertebra to be irradiated. A prerequisite for this type of treatment is that the applicator 10, or its guide region 13, respectively, is as long as possible, so that the site of irradiation can be reached at any time. A second prerequisite is that applicator 10, or its guide region 13, respectively, is as thin as possible, so that it can be guided through the drilled canal to the site of irradiation.

Figure 5:
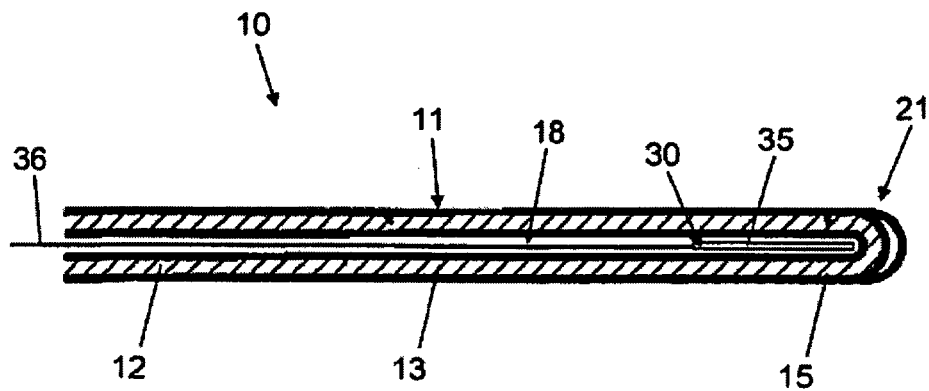
FIG. 5 shows the schematic sectional view of another embodiment of an applicator according to the invention.

Finally, an applicator 10 with a cylindrically shaped base body 11 is shown in FIG. 5, wherein foot region 12 as well as guide region 13 and head region 15 have the same outer diameter. Applicator 10 is formed as a particularly sterile, small feed tube. Radiation therapy device 30 has a radiation source unit 35, which is formed as a miniature x-ray source and is placed in head region 15 of applicator 10 in the region of its distal end 21. The radiation source unit 35 is connected to a supply cable 36 and is disposed in the inside space 18 of cylindrical base body 10* of applicator 10. The radiation is produced and also uniformly emitted in head region 15 of applicator 10 by means of the radiation source unit 35.

*sic; 11?—Translator's note

LIST OF REFERENCE NUMBERS

10 Applicator
11 Base body
12 Foot region
13 Guide region
14 Transition region
15 Head region
16 Support surface
17 Inner diameter of the guide region
18 Inside space of the guide region
19 Inside space of the foot region
20 Catch connection
21 Distal end of the base body
22 Proximal end of the guide region
30 Radiation therapy device
31 Housing
32 Uptake piece
33 Adapter
34 Front side of the uptake piece
35 Radiation source unit
36 Supply cable
L Length of the guide region
Da1 Outer diameter of the foot region
Da1* Outer diameter of the guide region
α Conical course of the transition region

*sic; Da2?—Translator's note

The invention claimed is:

1. A method for transporting radiation to a body region, said method comprising:
   forming a canal up to the body region, wherein said forming step comprises drilling or tissue punching the canal, the canal having a canal diameter, the canal diameter being substantially uniform,
   then, introducing an applicator which is fitted to the diameter of the canal into the canal in order to guide a probe tip or a radiation source unit, said applicator being shaped for use with a radiation therapy device for producing a defined radiation dose for irradiating the body region, wherein the applicator comprises a base body, the base body comprising a foot region for uptake of at least one component of a radiation therapy device and a cylindrical guide region connected thereto for uptake of a probe tip or a radiation source unit of a radiation therapy device, a distal end of the cylindrical guide region constituting a head region, said head region being a free end of the cylindrical guide region, wherein the cylindrical guide region of the applicator has an outer diameter which is fitted to the canal diameter, and
   introducing the probe tip or the radiation source unit into the applicator.

2. The method according to claim 1, wherein the canal is reinforced by a guide tube, at least in regions.

3. The method according to claim 1, wherein a transition region is formed between the foot region and the guide region.

4. The method according to claim 3, wherein whereby the diameter of the guide region is smaller than the diameter of the foot region and whereby the length of the guide region is longer than or equal to the length of the transition region.

5. The method according to claim 3, wherein the diameter of the guide region is equal to the diameter of the foot region and whereby the length of the guide region is longer than or equal to the length of the transition region.

6. The method according to claim 3, wherein the transition region has a conical course, at least in regions.

7. The method according to claim 3, wherein the transition region has a support surface, at least in regions, for at least one component of the radiation therapy device.

8. The method according to claim 7, wherein an inner surface of the guide region is directly connected to the support surface.

9. The method according to claim 1, wherein an inside space of the guide region is formed as a cylinder.

10. The method according to claim 4, wherein the ratio of the length of the guide region to an outer diameter of the guide region is greater by a multiple.

11. The method according to claim 1, wherein the applicator has at least one radiation filter element.

12. The method according to claim 1, wherein the applicator has at least one cooling element.

13. The method according to claim 1, wherein the radiation that is transported to the body region is produced by the radiation therapy device, wherein the radiation therapy device a comprises the radiation source unit.

14. The method according to claim 13, wherein the radiation source unit is introduced into the applicator and the radiation is emitted in the applicator.

15. The method according to claim 13, wherein the radiation source unit is joined with the probe tip for emitting radiation, and the probe tip is introduced into the applicator.

16. The method according to claim 13, wherein the radiation is produced via the radiation source unit, which is disposed in a housing for an uptake of the radiation source unit.

17. The method according to claim 16, wherein the housing has an uptake piece projecting from the housing for at least components of the probe tip or the radiation source unit.

18. The method according to claim 16, wherein the applicator is joined in a detachable manner with the housing via the foot region.

19. The method according to claim 16, wherein the applicator is joined in a detachable manner with the housing via an adapter.

20. The method according to claim 17, wherein a front side of the uptake piece is placed at a transition region of the applicator.

21. The method according to claim 20, wherein the front side of the uptake piece is placed adjacent to a proximal end of the guide region of the applicator.

22. A method for treating a vertebral body, said method comprising:
   drilling a hole in the vertebral body, the hole reaching up to a region to be treated, the hole having a hole diameter, the hole diameter being substantially uniform;

transporting radiation to the region to be treated, wherein said transporting comprises introducing an applicator which is fitted to the diameter of the drilled hole into the drilled hole, said applicator guiding a probe tip or a radiation source unit of a radiation therapy device, said applicator being shaped for use with a radiation therapy device for producing a defined radiation dose for irradiating a body region, wherein the applicator comprises a base body, the base body comprising a foot region for the uptake of at least one component of the radiation therapy device and a cylindrical guide region connected thereto for the uptake of the probe tip or the radiation source unit of the radiation therapy device, a distal end of the cylindrical guide region constituting a head region, said head region being a free end of the cylindrical guide region, wherein the cylindrical guide region of the applicator has an outer diameter which is fitted to the hole diameter, wherein radiation is produced by the probe tip or by the radiation source unit and is transported to the region to be treated by means of the applicator, and whereby, the region to be treated is irradiated with radiation;

after terminating a treatment of the vertebral body, removing the applicator from the drilled hole, and subsequently, stabilizing the vertebral body.

23. The method according to claim 22, wherein at least one section of the drilled hole is reinforced by a guide tube.

24. The method according to claim 22, wherein the vertebral body is stabilized by filling with bone cement.

25. The method according to claim 22, wherein after removal of the applicator from the drilled hole, the vertebral body can first be aligned by introducing a balloon catheter into the drilled hole and the vertebral body is subsequently stabilized by filling with bone cement.

* * * * *